(12) United States Patent
Schaub

(10) Patent No.: US 8,187,000 B2
(45) Date of Patent: May 29, 2012

(54) IMPRESSION CAP

(75) Inventor: Jörg Schaub, Lörrach-Brombach (DE)

(73) Assignee: Straumann Holding AG, Basel (CH)

( * ) Notice: Subject to any disclaimer, the term of this patent is extended or adjusted under 35 U.S.C. 154(b) by 139 days.

(21) Appl. No.: 12/009,308

(22) Filed: Jan. 17, 2008

(65) Prior Publication Data

US 2008/0176186 A1     Jul. 24, 2008

(30) Foreign Application Priority Data

Jan. 18, 2007   (EP) .................................... 07100717

(51) Int. Cl.
*A61C 8/00* (2006.01)

(52) U.S. Cl. ........................................ 433/173; 433/214

(58) Field of Classification Search .......... 433/172–174, 433/175–176, 177, 213–214, 201.1
See application file for complete search history.

(56) References Cited

U.S. PATENT DOCUMENTS

| | | | |
|---|---|---|---|
| 6,068,479 A * | 5/2000 | Kwan | 433/173 |
| 6,250,922 B1 * | 6/2001 | Bassett et al. | 433/172 |
| 6,332,777 B1 | 12/2001 | Sutter | |
| 6,382,977 B1 * | 5/2002 | Kumar | 433/173 |
| 6,461,160 B1 * | 10/2002 | Sutter | 433/173 |
| 6,561,805 B2 * | 5/2003 | Kumar | 433/174 |
| 6,790,040 B2 * | 9/2004 | Amber et al. | 433/173 |
| 2006/0228672 A1 | 10/2006 | Hurson et al. | |

FOREIGN PATENT DOCUMENTS

| | | | |
|---|---|---|---|
| EP | 1704829 A1 * | 9/2006 | |
| FR | 2690069 | * 10/1993 | |
| WO | WO 96/29019 | 9/1996 | |
| WO | WO 02/17814 A1 | 3/2002 | |

* cited by examiner

*Primary Examiner* — Cris L Rodriguez
*Assistant Examiner* — Edward Moran
(74) *Attorney, Agent, or Firm* — Scully, Scott, Murphy & Presser, P.C.

(57) ABSTRACT

A two-part impression cap for manufacturing a model for a dental implant, comprising: a cylindrical body and a cap-shaped part pluggable onto the cylindrical body, the cylindrical body and the cap-shaped part having a common central axis, the cap-shaped part being provided with elastic elements extending in the direction of the central axis, which elements are adapted to be bent towards the central axis and thus to create a tension in the elastic elements for engaging a groove in the interior of an abutment, adapter or the like, and the cylindrical body being adapted to fit tightly on the outside of the abutment, adapter or the like.

20 Claims, 4 Drawing Sheets

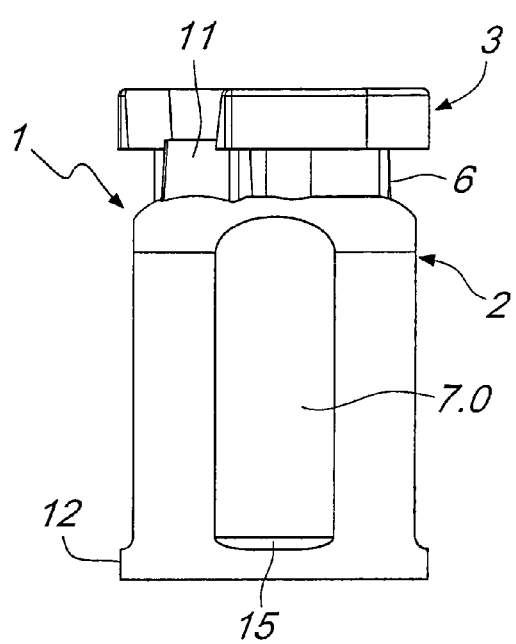
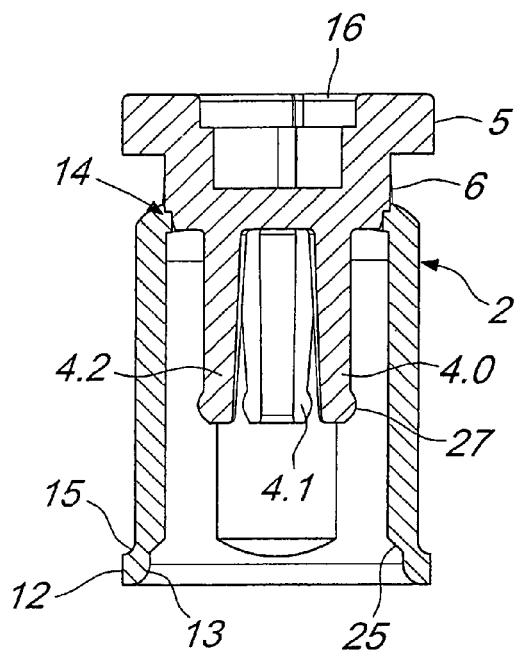
Fig. 1A   Fig. 1B
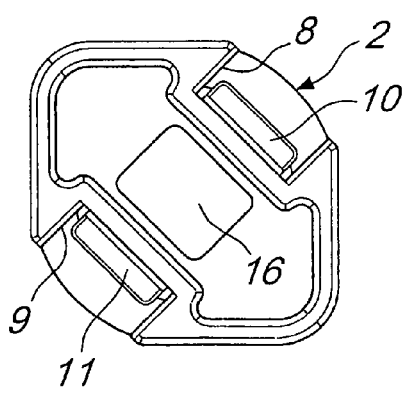
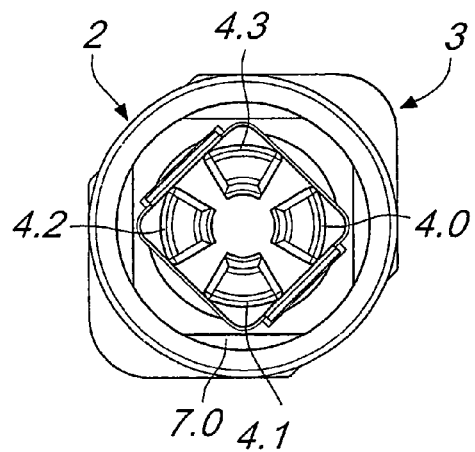
Fig. 1C   Fig. 1D

IMPRESSION CAP

CROSS REFERENCE TO RELATED APPLICATION

This application claims benefit of foreign priority of European Patent Application No. 07100717.3, filed Feb. 18, 2007, which is hereby incorporated by reference in its entirety.

The present invention refers generally to a two-part impression cap for manufacturing a model for implants, in particular dental implants, which is easy and inexpensive to produce, and is flexible to use.

BACKGROUND OF THE INVENTION

For manufacturing an impression of the dental area, impression caps have become widely known in dentistry. They are used in the procedure for manufacturing a dental prosthesis, an imprint of a patient's dental positions becoming possible by means of these impression caps, which is true to nature and adapted to the position and direction.

Dental implants are used to replace lost, damaged or unaesthetic teeth. This is done by means of an artificial dental prosthesis in order to restore the chewing ability or the aesthetic appeal within a patient's mouth.

For manufacturing such a dental prosthesis, the dentist first places a dental implant in the jaw bone. After successful healing of the implant in the jaw bone, either an abutment or a different suitable cap, in the following called prosthodontist's adapter for simplification, is provisionally placed onto the implant for fastening an impression cap thereon which transfers the direction and position of a dental model to be manufactured at a later stage to the impression model. Then the impression cap is placed onto the implant with the abutment or prosthodontist's adapter on top of it, and it is pressed onto the patient's jaw by means of a mold filled generally with a fast-setting impression compound (e.g. elastomers, silicone) for obtaining an imprint of the patient's teeth which is true to nature and geometrically correct.

During this process, the impression cap remains within the impression compound and is withdrawn from the jaw, together with the mold, after the impression compound has set. The plastic model created in this manner is used in the dental laboratory to precisely model the jaw and to produce an individual dental model. This conveying of the geometrical situation in the jaw onto a dental model, however, is extremely difficult, especially if the denture is positioned in the visible area, e.g. in the area of the front teeth, where aesthetic considerations are important. Minor deviations of the geometry, e.g. due to vibrations during the setting process during imprinting, have negative effects on the prosthodontist's mold to be produced and thus also on the dental prosthesis. The impression produced by the dentist is given to the prosthodontist as a base for manufacturing a plaster model of the jaw bone. In the laboratory, the prosthodontist places a provisional implant, in the following called prosthodontist's implant, having a suitable placed-on abutment or prosthodontist's adapter, onto the impression model with the impression cap located in it, which prosthodontist's implant is suited for modeling the implant positioned into the jaw and the dental prosthesis to be modeled on top of it. Thus, the prosthodontist's implant has the same position within the impression model as the implant placed into the patient's jaw bone. The geometrical relations within the patient's jaw can be modeled very precisely in this manner. Then the impression with the impression cap enclosed in it and the assembly of prosthodontist's implant and abutment on top of it is grouted with a plaster substance. After successful setting of the plaster substance, the impression mask is removed, and a complete plaster model of the patient's jaw with the prosthodontist's implant cast in is provided for further denture manufacturing.

Impression caps are known in various embodiments which have different shapes depending on the task of the dental model to be produced. Thus, impression caps adapted to the shape of the abutment are known which, however, have the disadvantage that the dentist must have a large number of impression caps in store for various geometries of the occlusal part of an abutment, in order to guarantee the precise adaptation to the abutment, since in case of exceedingly large clearances between the inner surface of the impression cap and the outer surface of the abutment's occlusal part, shifts of the impression cap can take place.

Also, impression caps with different fastening methods are known, such as impression caps which are screwed on or plugged on by means of a clamping device. Clamping-type impression caps generally have flexible portions on the side facing the implant, which portions can clamp the dental implant; however, they are insufficiently secured against torsions since the clamping only acts on the collar area of the abutment, and therefore they easily slide off in the clamp connection area. Such an impression cap is e.g. known from EP 0 680 732 B1.

Furthermore, an impression cap is known from U.S. Pat. No. 6,382,977 B1, which impression cap is provided with flexible thin-walled portions at its proximal end, which portions snappingly engage the implant's interior. The proximal end of the impression cap also has an adjustment recess or an adjustment hub for assuming a specific position in the implant's interior.

During manufacturing of such impression caps, it has been shown in practice that the production of an impression cap with the flexible portions provided on it for clamping or snapping onto the implant presents substantial problems during injection molding, since they must be manufactured with great precision. Due to this required precision, these injection-molding model forms are costly to produce; and in addition, it has been shown that manufacturing of these thin-walled structures is extremely difficult.

SUMMARY OF THE INVENTION

The aim of the present invention is therefore to provide an impression cap for producing the model of a dental implant which avoids the problems mentioned above.

Within this aim, it is a special object of the present invention to implement an impression cap for producing the model of a dental implant which is substantially lighter and less costly to produce.

Additionally, a special object of the present invention consists in enabling a plurality of various combination possibilities of the cylindrical body and the cap-shaped part for producing the model of a dental implant.

Furthermore, an object of the present invention is to implement an impression cap which is easy to handle.

This aim and these and other objects to be found in the following specification are fulfilled by an impression cap according to appended Claim 1. Advantageous further features of the present invention are a subject matter of the dependent claims.

BRIEF DESCRIPTION OF THE DRAWINGS

Other features and advantages of the present invention as well as the mode of operation of the exemplary embodiments of the present invention are described below with reference to the accompanying drawings. These drawings exemplify the present invention and are further used, together with the specification, to explain the principles of the invention and enable a person skilled in the art to manufacture and use the invention.

In the drawings:

FIG. 1A shows a side view of a two-part impression cap according to a preferred embodiment of the invention;

FIG. 1B shows a side view of the two-part impression cap of FIG. 1A in full section;

FIG. 1C shows a top view of the two-part impression cap of FIG. 1A;

FIG. 1D shows a bottom view of the two-part impression cap of FIG. 1A;

DESCRIPTION OF THE PREFERRED EMBODIMENTS

Figure 2A:
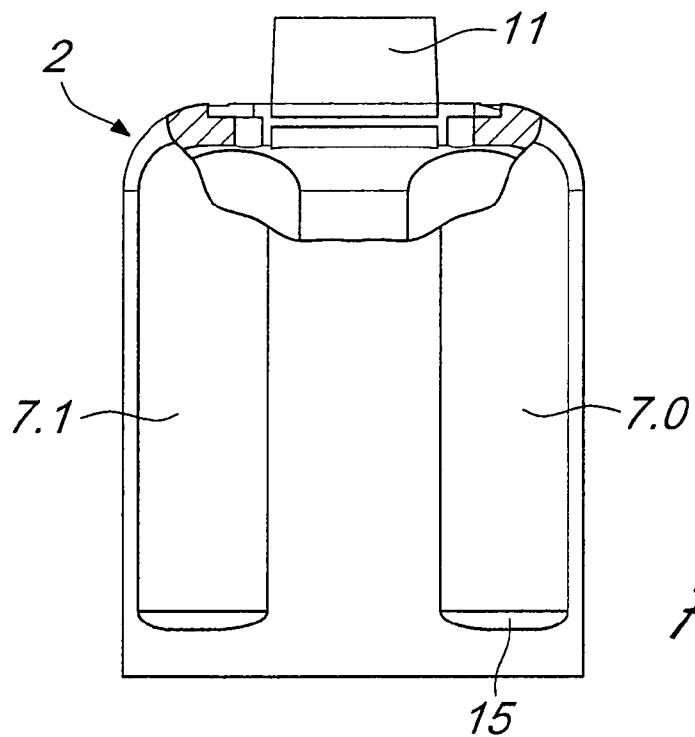
FIG. 2A shows a side view of a cylindrical body of the two-part impression cap of FIG. 1A.

With reference to the FIGS. 1A through 4, a preferred embodiment of an impression cap is described. The impression cap 1 for manufacturing a model for a dental implant comprises a cylindrical body 2 and a cap-shaped part 3 which can be plugged onto the cylindrical body 2, the plug-on cap-shaped part 3 being provided with a plurality of fingers 4.0, 4.1, 4.2, 4.3 (in the following identified by reference number 4 for the sake of simplicity and also called elastic means), which engage the interior of the cylindrical body 2.

Figure 2B:
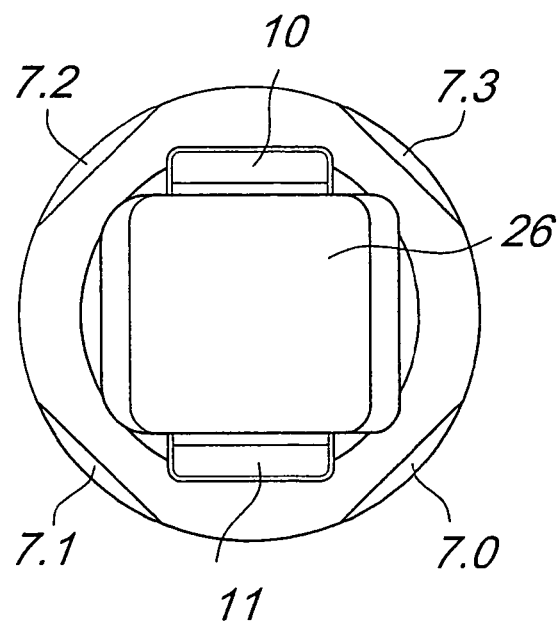
FIG. 2B shows a top view of the cylindrical body of FIG. 2A.

In the assembled condition, the upper cap-shaped part 3 protrudes through a square opening 26, see FIG. 2B, into the cylindrical body 2. The cap-shaped part 3 has a web portion 6 on which, in the assembled condition, elevations or protrusions 10, 11 of the cylindrical body 2 extend. In the assembled condition, the lower part of the web portion 6 touches a step-shaped portion 14 of the cylindrical body 2. For better stabilization of the two-part impression cap 1 during assembly, the step-shaped portion 14 can advantageously be provided with an adhesive.

From the web portion 6, the fingers 4 extend in the axial direction downward, which fingers extend by typically approximately 50-70%; and more typically by approximately 60% of the axial extension of the cylindrical body 2 into the hollow interior of the cylindrical body 2. The plurality of fingers 4 are made of an elastic material, and their diameter tapers towards the end.

This embodiment of the fingers 4 allows good bending behavior as well as stability. Also, this embodiment allows easy manufacturing of the injection mold form, since no extremely fine structures have to be injection-molded. The fingers 4 are arranged symmetrically at equal distances around the central axis.

The cylindrical body 2 surrounding the portion of the fingers 4 is provided advantageously in the proximal area on its outer surface with a plurality of drum magazine-like milled recesses 7.0 through 7.3 (in the following identified by reference number 7 for the sake of simplification) for providing a resistance against torsion or slipping during impressing in the viscid impression compound, such as polymers or hard plaster, during the molding process within the patient's mouth. On the lower side of the milled recess 7, there is a narrow semicircular bench 15 which transitions to a cylindrical portion 12.

In an advantageous embodiment of the invention, the plurality of milled recesses 7 are arranged symmetrically radially on the outer surface of the cylindrical body 2. These milled recesses 7 run parallel to the longitudinal axis at equal distances and are curved along the semicircular bench 15 before transitioning into the surface of the cylindrical area 12. On the opposite side of the cylindrical area 12, an inner bottom edge 13 curved towards the body interior is located on the interior of the cylindrical body 2 and transitions to an incline 25 of approximately 45 degrees. The incline 25 is provided as a clearance to enable the transition between the different diameters.

FIGS. 2A and 2B show the cylindrical body 2 in the non-assembled condition, with the milled recesses 7 running symmetrically to the central axis of the square opening 26 which is provided for inserting the fingers 4 of the cap-shaped part 3.

Figure 3A:
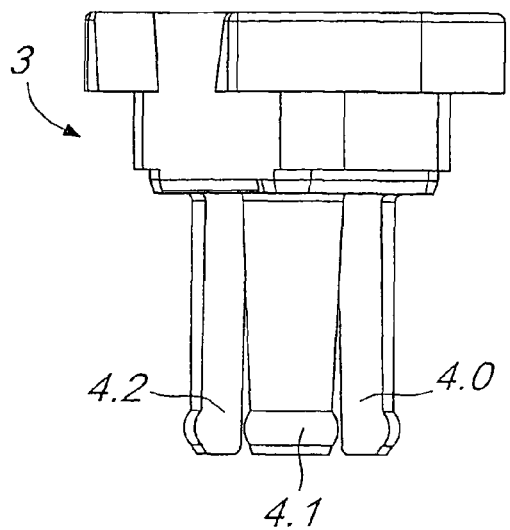
FIG. 3A shows a side view of the cap-shaped part of the two-part impression cap of FIG. 1A.
Figure 3B:
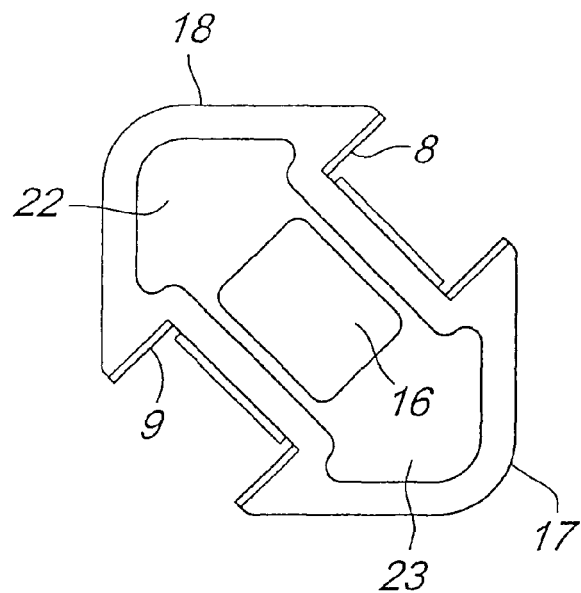
FIG. 3B shows a top view of the cap-shaped part of FIG. 3A.
Figure 3C:
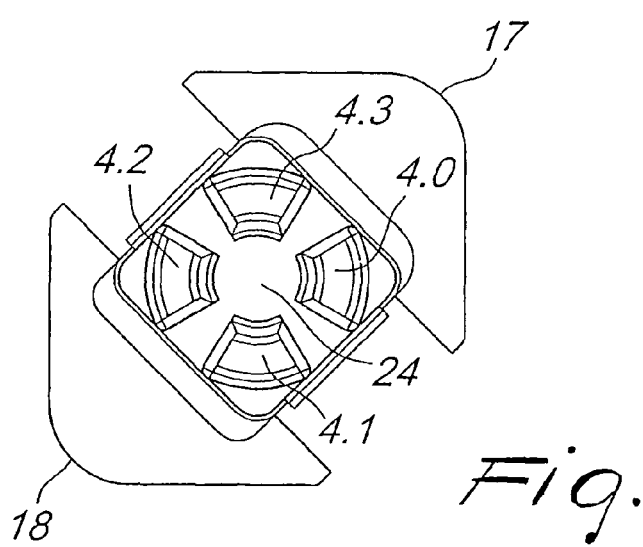
FIG. 3C shows a bottom view of the cap-shaped part of FIG. 3A.

FIGS. 3A through 3C show the cap-shaped part 3 in the non-assembled condition, where the plurality of the fingers 4, which are made of an elastic material, can be bent in the central axis area during application of pressure, e.g. during pressing into an abutment 21, an adapter (not shown) or the like towards the central axis, thus generating a tension in the material which can advantageously be used to fix the part to a body.

Advantageously, the diameter of the individual fingers 4 is larger in the web portion 6 than in the area of the tips of the fingers 4, which first causes a high rigidity in the web portion 6 and secondly presses the cylindrical body onto the abutment.

In the area surrounded by the radially arranged fingers 4, a partially open exposed, ring-shaped area 24 is formed defining a free space which therefore leaves sufficient clearance during application of pressure, e.g. when the cap-shaped part 3 is inserted through the cylindrical body 2, to the fingers 4, so as to enable a snap connection with a groove 19 provided for this purpose in the interior of an abutment 21 or prosthodontist's adapter.

On one end forming the lower area of the finger 4, an outwardly protruding portion, a curvature 27, is provided on each of the fingers 4, suitable for engaging e.g. a corresponding groove 19 in an abutment 21 or a prosthodontist's adapter (not shown). In a preferred embodiment, this curvature is embodied as an outwardly curved, semicircular surface. It can take different shapes, depending on the requirements made on individual abutments.

The other end of the finger 4 borders on a head 5 of the cap-shaped part 3 with a substantially square cavity 16 which has on its outer surface in the area which engages during assembly the cylindrical body 2, the step-shaped area 14. This step-shaped area 14 can advantageously be provided, as mentioned above, with an adhesion means, e.g. glue, to provide the impression cap 1 with additional stability and strength.

On two opposed sides of the square cavity 16, there are rectangular recesses 8, 9 wider than the corresponding sides of the square cavity 16. On the two other sides of the square cavity 16, there are adjacent triangular areas 22, 23 with rounded tips 17, 18. The end face of the cap-shaped part 3 thus has a structure similar to a double arrow. This structure causes a withdrawal of the impression mold to effect a retention of the impression compound which has flowed in between the web portion 6 of the cap-shaped part 3 and the cylindrical body 2, thus preventing a torsion of the impression cap 1.

Figure 4:
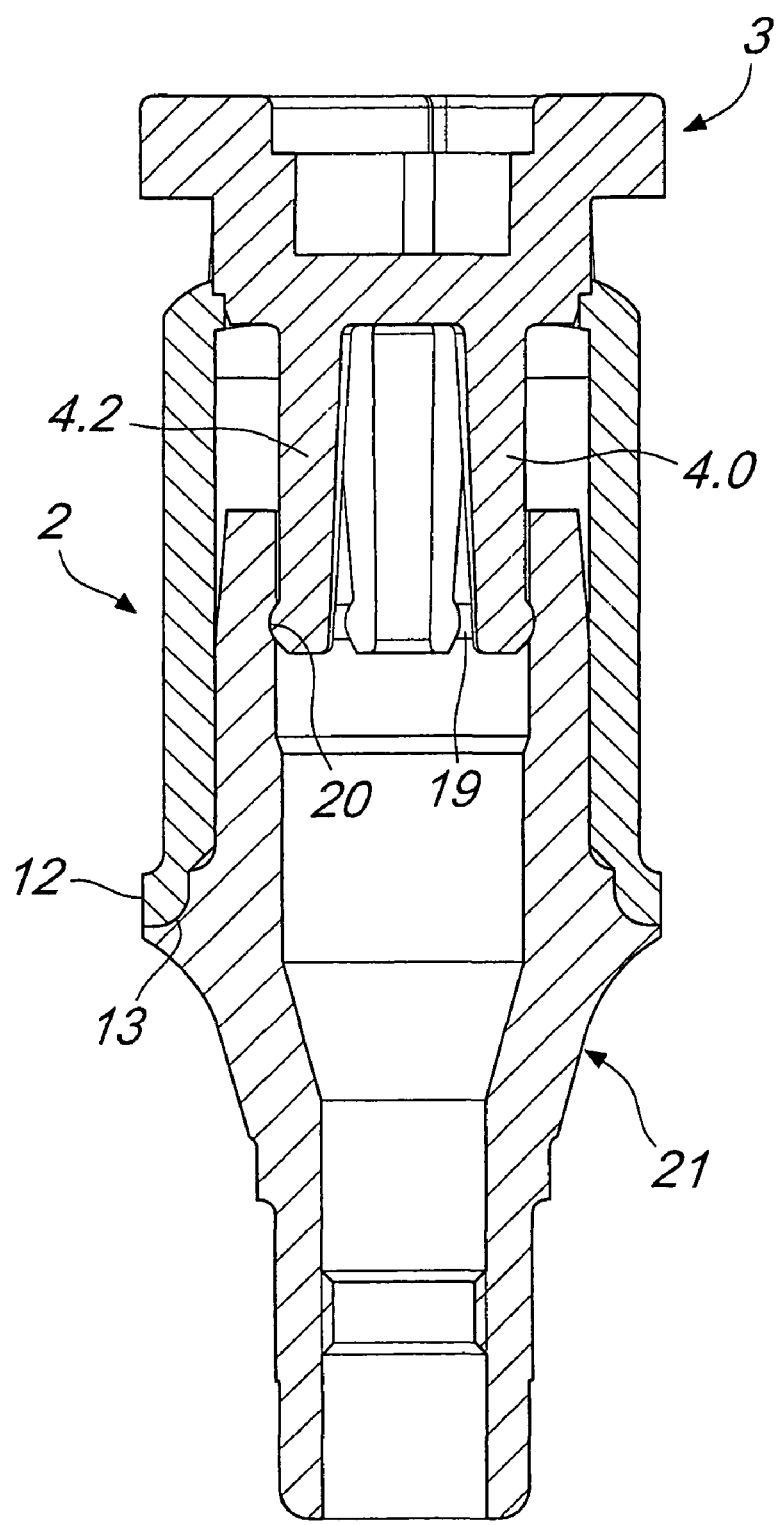
FIG. 4 shows a side view of the two-part impression cap according to the invention, placed on an abutment, in half-section.

FIG. 4 shows a two-part impression cap 1 mounted on an abutment 21 or a prosthodontist's adapter (not shown), the cylindrical body 2, together with the cap-shaped part 3 placed on top of the body, being fixed to the abutment 21 by means of a snap connection. The cap-shaped part 3 engages through the square opening 26 of the cylindrical body 2 with the area of the fingers 4 and clicks into place in the groove 19 on the inner surface of the abutment 21. In the preferred embodiment, the groove 19 is ring-shaped and at the contact surface 20, where the curvature 27 and the abutment 21 snap together, advantageously semicircular.

The tension which builds up in the fingers' material when the fingers 4 are pressed into the interior of the abutment 21 ensures a form-locking pressure of the curved inner bottom edge 13 in the collar area of the abutment 21 and at the same time stabilizes the upper area of the impression cap against torsion or tilting movements since the catching of the fingers 4 in the groove 19 of the abutment 21 exerts additional tension on the contact surface 20 of the ring-shaped groove 19.

Although in the preferred embodiment, the invention is provided with four fingers on the cap-shaped part, the person skilled in the art will readily understand that the same advantages also apply with a different number of fingers, where in practice, good results were also achieved with three, five or more fingers. Indeed, as the person skilled in the art will understand, the number of fingers can be varied as long as a stable attachment of the cap-shaped part 3 to the abutment 21 can be guaranteed.

Since the cap-shaped part 3 can advantageously be placed separately into the cylindrical body 2 by means of a snap connection, the cap-shaped part 3 or the cylindrical body 2 can be replaced quickly and easily for individual adaptation to special abutments 21 or prosthodontist's adapters without the use of auxiliaries or special tools, e.g. screwdrivers.

The disclosures in EPA 07100717.3 from which this application claims priority are incorporated herein by reference.

What is claimed is:

1. A two-part impression cap for manufacturing a model for a dental implant, comprising:
    a cylindrical body, and
    a cap-shaped part pluggable onto the cylindrical body,
    the cylindrical body and the cap-shaped part having a common central axis, the cap-shaped part being provided with a web portion, from which elastic radially arranged fingers extending in the direction of the central axis, adapted to be bent towards the central axis and to thus create a tension in the elastic radially arranged fingers for engaging a groove in the interior of an abutment, or an adapter,
    wherein the cylindrical body is provided with at least two elevations which, in the assembled condition, extend into the web portion, and is adapted to fit tightly on the outside of the abutment, or on the adapter.

2. The two-part impression cap according to claim 1, wherein the elastic radially arranged fingers are arranged at equal distances around the central axis.

3. The two part impression cap according to claim 1, wherein the elastic radially arranged fingers are provided with respective curvatures at the height of said corresponding groove.

4. The two part impression cap according to claim 1, wherein the cylindrical body is provided, in it apical area, with a bottom edge exerting a form-locking pressure on a collar area of the abutment or on the adapter.

5. The two-part impression cap according to claim 1, wherein the cylindrical body is provided with milled recesses on the outside.

6. The two-part impression cap according to claim 1, wherein the cap-shaped part is provided with at least two recesses.

7. The two-part impression cap according to claim 6, wherein the two elevations protrude into the recesses.

8. The two-part impression cap according to claim 1, wherein the end face of the cap-shaped part is provided with at least two opposed triangular areas.

9. The two-part impression cap according to claim 1, wherein between the radially arranged fingers a partially open exposed, ring-shaped area is provided.

10. The two-part impression cap according to claim 1, wherein the radially arranged fingers protrude approximately 50-70% into the interior of the cylindrical body in the axial direction.

11. A combination of an abutment or an adapter adapted for attachment to a dental implant, and a two-part impression cap for manufacturing a model for a dental implant, the abutment or adapter comprising a collar area and a central bore, the impression cap comprising:
    a cylindrical body, and
    a cap-shaped part pluggable onto the cylindrical body,
    the cylindrical body and the cap-shaped part having a common central axis,
    the cap-shaped part being provided with a web portion and elastic radially arranged fingers extending in the direction of the central axis, adapted to be bent towards the central axis and to thus create a tension in the elastic radially arranged fingers for engaging a ring-shaped groove in the interior of the central bore of the abutment, or adapter, and
    wherein the cylindrical body is provided with at least two elevations which, in the assembled condition, extend into the web portion, and is adapted to fit tightly on the outside of the abutment or adapter.

12. The combination according to claim 11, wherein the elastic radially extending fingers are arranged at equal distances around the central axis.

13. The combination according to claim 11, wherein the elastic radially arranged fingers are provided with respective curvatures at the height of said corresponding groove.

14. The combination according to claim 11, wherein the cylindrical body is provided with milled recesses on the outside.

15. The combination according to claim 14, wherein the at least two elevations are on a surface facing the cap-shaped part and wherein the cap-shaped part is provided with at least two recesses facing the cylindrical body.

16. The combination according to claim 15, wherein the two elevations protrude into the recesses facing the cylindrical body.

17. The combination according to claim 11, wherein the end face of the cap-shaped part is provided with at least two opposed triangular areas.

18. The combination according to claim 11, wherein between the radially arranged fingers, there is provided a partially open exposed, ring-shaped area.

19. The combination according to claim 11, wherein the radially arranged fingers protrude approximately 50-70% into the interior of the cylindrical body in the axial direction.

20. The combination according to claim 11, wherein an inner bottom edge of the cylindrical body is curved inwardly, and wherein the bottom edge transitions to an incline located within a collar area of the abutment.

* * * * *